United States Patent [19]
Long et al.

[11] Patent Number: 6,069,485
[45] Date of Patent: May 30, 2000

[54] C-V METHOD TO EXTRACT LATERAL CHANNEL DOPING PROFILES OF MOSFETS

[75] Inventors: Wei Long, Sunnyvale; Yowjuang W. Liu; Chun Jiang, both of San Jose, all of Calif.

[73] Assignee: Advanced Micro Devices, Inc., Sunnyvale, Calif.

[21] Appl. No.: 09/237,539

[22] Filed: Jan. 26, 1999

[51] Int. Cl.$^7$ ...................................................... H01L 29/78
[52] U.S. Cl. ............................................................ 324/769
[58] Field of Search .................................... 324/765, 769, 324/719, 158.1, 689, 662, 663, 671; 257/48, 268, 335, 408

[56] References Cited

U.S. PATENT DOCUMENTS 5,194,923  3/1993  Vinal ........................................ 257/268

OTHER PUBLICATIONS

On the Accuracy of Channel Length Characterization of LDD MOSFET's, Jack Y. –C. Sun, Matthew R. Wordeman, Stephen E. Laux, 1986, 7 pages (month unavailable).

An Accurate Gate Length Extraction Method for Sub–Quarter Micron MOSFET's, Cheng–Liang Huang, John V. Faricelli, Dimitri A. Antoniadis, Nadim A. Khalil, Rafael A. Rios, 1996, 6 pages (unavailable month).

A Problem–Specific Inverse Method for Two–Dimensional Doping Profile Determination from Capacitance–Voltage Measurements, G. J. L. Ouwerling, 1991, 18 pages (month unavailable).

The Extraction of Two–Dimensional MOS Transistor Doping via Inverse Modeling, Nadim Khalil, John Faricelli, David Bell, Siegfried Selberherr, 1995, 3 pages (month unavailable).

A New "Shift and Ratio" Method for MOSFET Channel–Length Extraction, Yuan Taur, D.S. Zicherman, D.R. Lombardi, Phillip J. Restle, C.H. Hsu, Hussein I. Hanafi, Matthew R. Wordeman, Bijan Davari, Ghavam G. Shahidi, 1992, 3 pages (month unavailable).

CMOS Circuit Design, Layout, and Simulation, R. Jacob Baker, Harry W. Li, David E. Boyce, 1997, 5 pages (month unavailable).

A New Capacitance Measurement Method for Lateral Diffusion Profiles in Mosfet's with Extremely Short Overlap Regions, H. Uchida, Y. Kajita, K. Fukuda, J. Ida, N. Hirashita, K. Nishi, publication date unknown, 2 pages (month unavailable).

*Primary Examiner*—Vinh P. Nguyen
*Attorney, Agent, or Firm*—LaRiviere, Grubman & Payne, LLP

[57] ABSTRACT

A method and apparatus that uses gate-to-substrate capacitance with varying amounts of source/drain junction bias to measure channel lateral doping profile by applying a series of different voltages between the source/drain and the substrate. The gate capacitance is measured for the different voltages. The capacitance is used to calculate the depletion width. From the depletion width, channel doping is calculated. Using this method direct evidence of a localized Boron pile up at source/drain edge is shown.

16 Claims, 7 Drawing Sheets

C-V METHOD TO EXTRACT LATERAL CHANNEL DOPING PROFILES OF MOSFETS

TECHNICAL FIELD

The present invention relates to apparatus and methods for determining lateral distribution of dopants along the channel of MOS transistors in the sub-quarter micron regime. More particularly, the present invention relates to apparatus and methods for determining lateral distribution of dopants along the channel of MOS transistors in the sub-quarter micron regime using gate-to-substrate capacitance behavior. Even more particularly, the present invention relates to apparatus and methods for determining lateral distribution of dopants along the channel of MOS transistors in the sub-quarter micron regime using information relating to voltage bias dependence of gate-to-substrate capacitance $C_{gb}$.

BACKGROUND ART

As MOS transistors are scaled to the sub-quarter micron regime, the lateral distribution of dopants along the channel becomes a critical factor affecting their operation and performance. A technique that allows one to obtain the lateral doping profile is therefore indispensable. Vertical profiling techniques such as the C–V and SIMS have widely been used. The vertical C–V methods assumes a uniform lateral doping of channel and substrate regions, while the SIMS method is not feasible for submicron channel lengths. Lateral techniques for small size transistors, however, have met with less success. N. Khalil et al. in IEEE EDL-16(1), G. J. L. Ouwerling in Solid State Electronics., vol 34, p. 197, 1991 and Lee et al. in IEDM'97 Proceedings teach inverse modeling approach techniques by finding a lateral doping profile using an iterative procedure. Basically, these approaches determine whether the C–V/I–V characteristics of an assumed lateral doping profile matches the measured C–V/I–V characteristics of a device under test. However, none of these approaches teach, suggest, nor motivate how to accurately extract lateral doping profile directly from the measured data of the device under test.

Accordingly a need is seen to exist for a method for determining the non-uniform lateral surface doping for sub-micron CMOS devices directly from C–V measurements of the device, which is simple, nondestructive and accurate.

DISCLOSURE OF INVENTION

It is therefore a primary object of the present invention to provide a method and system for determining the non-uniform lateral surface doping for sub-micron CMOS devices directly from C–V measurements of the device. Even more particularly, the present invention relates to apparatus and methods for determining lateral distribution of dopants along the channel of MOS transistors in the sub-quarter micron regime using bias dependence of gate-to-substrate capacitance $C_{gb}$ in accumulation to obtain channel doping concentration and its variations along the channel.

Accordingly, the foregoing objects are accomplished by taking advantage of a relationship that exists in short channel (sub-quarter micron) semiconductor devices, namely that the gate length is proportional to the gate-to-substrate capacitance $C_{gb}$. In general, $C_{gb}$ data of a short channel device contains the lateral source/drain substrate junction depletion width variation information at different source/drain substrate bias voltages. The above capacitance and length relationship means that shifts in $C_{gb}$ vs. source/drain substrate voltage ($V_{sb}/V_{db}$) can translate directly into the variations of the substrate junction depletion width (W) vs. $V_{sb}/V_{db}$. Consequently, information about the channel doping profile is contained in the $C_{gb}$ vs. V behavior. In accordance with the method of the present invention, the extraction of the channel doping profile starts with setting up a reference for length calculations by employing a large gate capacitor (e.g. 100×100 $\mu$m) to get the capacitance per unit area in accumulation regime. Then, the $C_{gb}$ of the sub-micron device being tested is measured at different drain/source bias voltages. Then, these $C_{gb}$ values are compared with the unit area $C_{gb}$ of the large area capacitor. The depletion width W at a given bias voltage is determined from comparing the sub-micron devices $C_{gb}$ values with the unit area $C_{gb}$ reference value measurement of a large capacitor. After that, $C_{gb}$–$V_{db}$ slope is extracted and used to calculate the channel doping using depletion relation:

$$N_{ch} = \frac{\varepsilon_s}{qW\dfrac{dW}{dV}} \qquad \text{Equation 1}$$

derived from equations (18c) and (18d) on page 81 of "The Physics of Semiconductor Devices" 1981 by S. M. Sze, where $N_{ch}$ is channel doping concentration, $\varepsilon_s$ the silicon dielectric permitivity and q the electron charge.

Other features of the present invention are disclosed or apparent in the section entitled: "BEST MODE FOR CARRYING OUT THE INVENTION.

BRIEF DESCRIPTION OF DRAWINGS

For fuller understanding of the present invention, reference is made to the accompanying drawing in the following detailed description of the Best Mode of Carrying Out the Present Invention. In the drawing.

Figure 1:
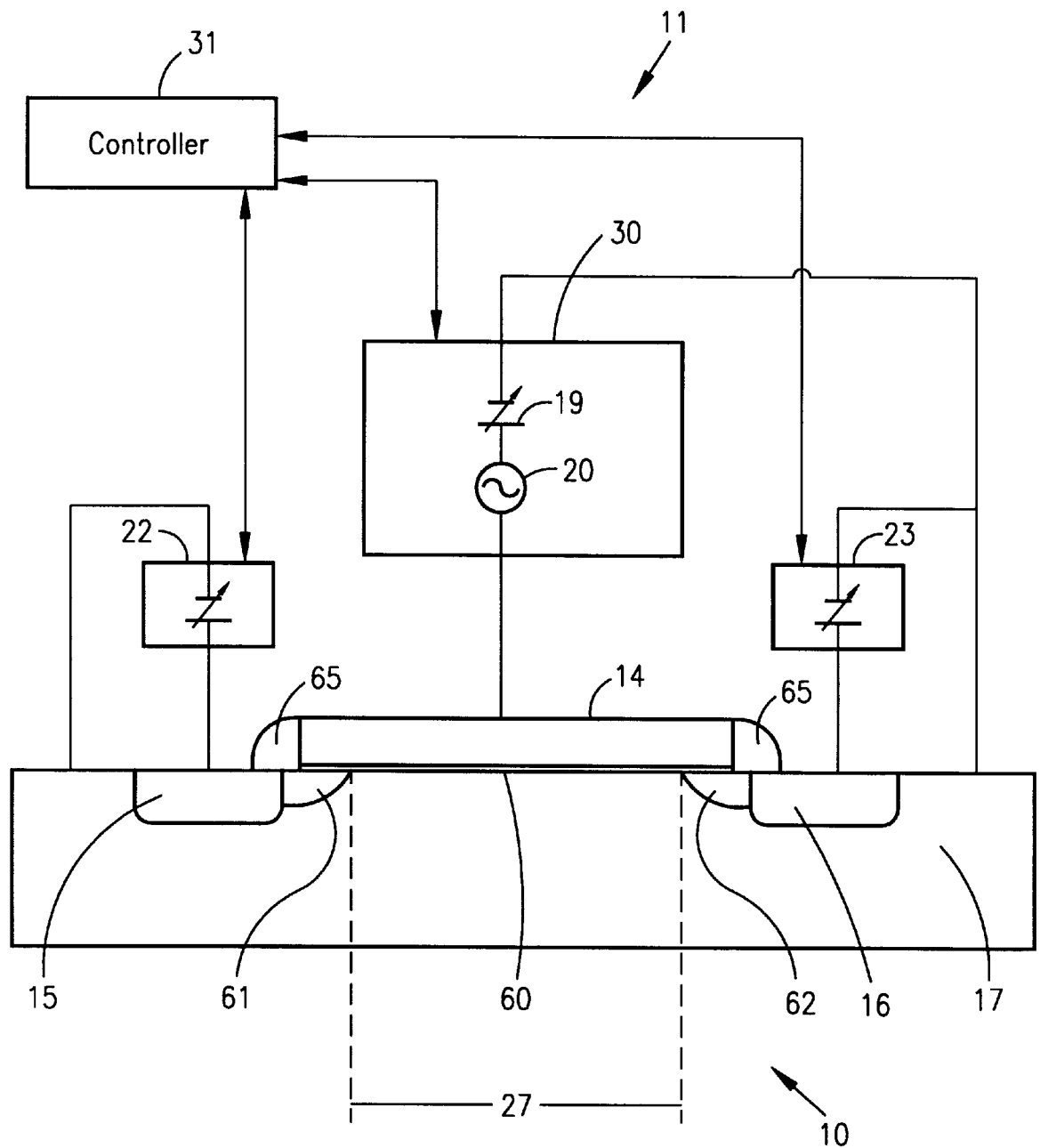
FIG. 1 is a schematic illustration of the apparatus used in the practice of the invention.

Reference numbers refer to the same or equivalent parts of the present invention throughout the several figures of the drawing.

BEST MODE FOR CARRYING OUT THE INVENTION

Experimental Setup and Measurements

Conventional 0.18 $\mu$m MOSFETs are employed in this work. Here, devices with halo and non-halo implantation are chosen to illustrate the application of the proposed method. Devices with halo implantation are created by implanting extra dopants into the channel with a tilted angle after the gate formation.

FIG. 1 depicts a MOS transistor 10 attached to a testing device 11 used to practice the invention. The MOS transistor 10 comprises a gate 14, a source 15, and a drain 16 mounted on a substrate 17. The gate 14 is separated from the substrate 17 by a thin insulating layer 60, which is formed by a thin oxide layer. Spacers 65 are placed on opposite ends of the gate 14. A source extension 61 extends from the source 15 to a point under the gate 14 so that the gate 14 overlaps with part of the source extension 61 by a source overlap length. A drain extension 62 extends from the drain 16 to a point under the gate 14 so that the gate 14 overlaps with part of the drain extension 62 by a drain overlap length. An effective gate length 27 ($L_{eff}$) extends from an end of the source extension 61 to an end of the drain extension 62, so that the gate length ($L_{MET}$) is the sum of the drain overlap length, the source overlap length, and the effective gate length 27.

The test device 11 uses an LCR meter 30. The LCR meter has a variable DC power source 19 and a AC source 20 in series with the DC source 19. A source variable DC power supply 22 is electrically connected between the source 15 and the substrate 17, and a drain variable DC power supply 23 is electrically connected between the drain 16 and the substrate 17. A controller 31 is electrically connected to the LCR meter 30, the source variable DC power supply 22, and the drain variable DC power supply 23. In the preferred embodiment a precision LCR meter (e.g. HP 4284 A) is used as a combined LCR meter 30 and controller 31 in single unit.

In operation, large area gate capacitors (e.g. 100×100 $\mu$m) are employed to determine by experimentation the capacitance per unit of length $C_{ox}$ of the type of gate being measured. The capacitance per unit length $C_{ox}$ is entered into the controller 31. Throughout the measurements, a calibration structure is employed to zero out all the parasitic capacitances due to probing pad and wiring. By using HP4284 LCR meter the resolution of the measurement setup is better than 0.1 fF.

Figure 2A:
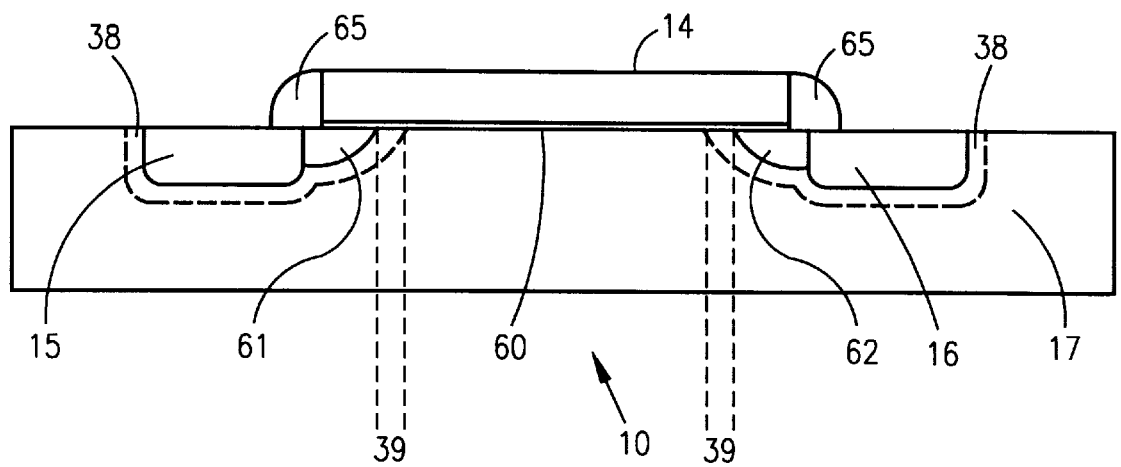
FIGS. 2a, 2b, and 2c are schematic illustrations of a MOS transistor which is tested in the device illustrated in FIG. 1 using a first method.
Figure 2B:
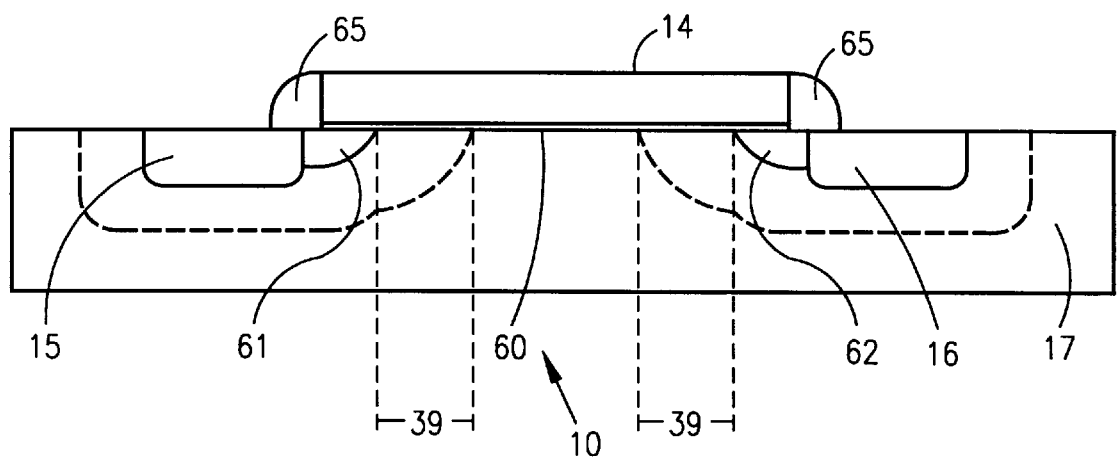
Figure 2C:
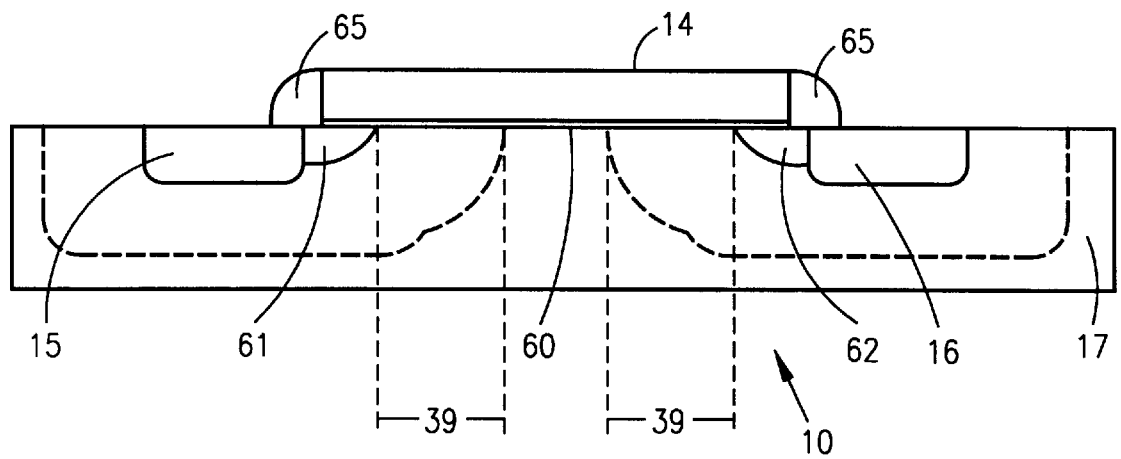

The controller 31 signals the LCR meter 30 to apply a set gate voltage $V_G$ to the gate. A fixed voltage is applied between the gate and the substrate. The absolute value of the fixed voltage applied between the gate 14 and substrate 16 $V_{Gb}$ is less than the absolute value of the threshold voltage $V_T$ of the MOS transistor 10, expressed as, $|V_{Gb}| \leq |V_T|$. The LCR meter 30 and controller 31 then measure and record the capacitance $C_{gb}$ (the capacitance between the gate 14 and the substrate 16, which is generated across the channel) for different voltages applied to the source and the drain. FIGS. 2a, 2b and 2c are schematic illustrations of the transistor 10 shown in FIG. 1 with depletion regions generated by different drain/source (meaning source or drain) to substrate voltages $V_{SB}/V_{DB}$. The testing setup is not shown to simplify the figures. The transistor 10 being tested in this example is an NMOS. In an NMOS transistor, the drain/source depletion region shrinks with an applied negative drain/source to substrate voltage $V_{SB}/V_{DB}$ and expands with and applied positive drain/source to substrate voltage $V_{SB}/V_{DB}$. In a PMOS transistor, the opposite behavior will be observed. In the example shown in FIGS. 2a, 2b, and 2c the voltage applied to the source $V_{SB}$ is set to equal the voltage of the drain $V_{DB}$ through the testing, so that for these examples the voltage between the source and substrate $V_{SB}$ and the voltage between the drain and the substrate $V_{DB}$ are represented by a single notation $V_{SD}$.

The controller 31 signals the source variable DC power supply 22 and the drain variable DC power supply 23 to apply a series of increasing voltages, which increases the lengths of the depletion regions 39 adjacent to the source 15 and the drain 16, as shown in FIGS. 2a, 2b, and 2c. FIGS. 2a, 2b, and 2c illustrate depletion regions 39 for the i-1, i, and i+1 values of the series of increasing voltages.

The controller 31 signals the source variable DC power supply 22 and the drain variable DC power supply 23 to set the source/drain to substrate voltage to $V_{SD}(i-1)$, which causes the depletion regions 38 adjacent to the source 15 and the drain 16, as shown in FIG. 2a. The width of the depletion regions for $V_{SD}(i-1)$ is notated as W(i-1), with the width of the depletion region being the sum of the lengths of the depletion regions 39. The controller 31 then signals the LCR meter 30 to measure the gate capacitance $C_{gb}(i-1)$, which is recorded by the controller 31.

The controller 31 signals the source variable DC power supply 22 and the drain variable DC power supply 23 to increase the source/drain voltage to $V_{SD}(i)$, which increases the lengths of the depletion regions 39 adjacent to the source 15 and the drain 16, as shown in FIG. 2b. The width of the depletion regions for $V_{SD}(i)$ is notated as W(i), with the width of the depletion region being the sum of the lengths of the depletion regions 39. The controller 31 then signals the LCR meter 30 to measure the gate capacitance $C_{gb}(i)$, which is recorded by the controller 31.

The controller 31 signals source variable DC power supply 22 and the drain variable DC power supply 23 to increase the source/drain voltage to $V_{SD}(i+1)$, which increases the lengths of the depletion regions 39 adjacent to the source 15 and the drain 16, as shown in FIG. 2c. The width of the depletion regions for $V_{SD}(i+1)$ is notated as W(i+1), with the width of the depletion region being the sum of the lengths of the depletion regions 39. The controller 31 then signals the LCR meter 30 to measure the gate capacitance $C_{gb}(i+1)$, which is recorded by the controller 31.

One way of determining effective channel length $L_{eff}$ is by setting $V_{SD}$ to the maximum negative value so that there is no depletion region. Then effective channel length $L_{eff}$ is defined as the length of the channel $L_C$. Using the measured gate capacitance $C_{gb}(x)$ the controller is able to determine the channel length $L_c(x)=C_{gb}(x)/C_{ox}$ (Equation 2). $L_{eff}=L_c(x)$ when there is no depletion region. There are other ways of determining the effective channel length, such as the method described in "A New 'Shift and Ratio' Method for MOSFET Channel-Length Extraction", by Yuan Taur et al., IEEE Electron Device Letters. Vol 13, No: 5, May 1992, which can be used here, instead.

For $V_{SD}(x)$, the width of the depletion region 39 W(x)=$L_{eff}-L_c(x)$, so that for $V_{SD}(i-1)$, W(i-1)=$L_{eff}-L_c(i-1)$, and for $V_{SD}(i)$, W(i)=$L_{eff}-L_c(i)$, and for $V_{SD}(i+1)$, W(i+1)=$L_{eff}-L_c(i+1)$.

Starting with the general equation W(x)=$L_{eff}-L_c(x)$ (Equation 3), we get:

$$\frac{dW}{dV_{SD}} = -\frac{dL_c}{dV_{SD}} \qquad \text{Equation 4}$$

For the point $V_{SD}(i)$, $dL_c/dV_{gd}$ can be estimated as:

$$\frac{dL(i)_c}{dV(i)_{SD}} \cong \frac{\Delta L(i)_c}{\Delta V(i)_{SD}} \cong \frac{L_c(i-1)-L_c(i+1)}{V_{SD}(i-1)-V_{SD}(i+1)} \qquad \text{Equation 5}$$

The controller 31 is then able to solve Equation 1 for $N_{ch}(i)$. The controller continues to take readings until the depletion regions of the source and drain contact each other so that the channel length $L_c$ approaches zero and the gate capacitance $C_{gb}$ drops abruptly.

The controller 31 calculates $N_{ch}(x)$ for every measured $V_{SD}(x)$. Assuming that the lateral doping profile is symmetric about the center of the gate, the controller 31 is able to calculate the doping profile at a distance x from and end of the gate.

In another embodiment of the invention using the same testing device at different settings in a different manner, the controller 31 signals the source variable DC power supply 22 output voltage $V_{SB}$ to always be set to the maximum negative value so that there is no depletion region around the source 15. The controller 31 signals the LCR meter 30 to apply a set gate voltage $V_G$ to the gate. The LCR meter 30 and controller 31 then measure and record the capacitance $C_{gb}$ (the capacitance between the gate 14 and the substrate 16, which is generated across the channel) for each different drain to substrate voltage $V_{DB}$.

Figure 3A:
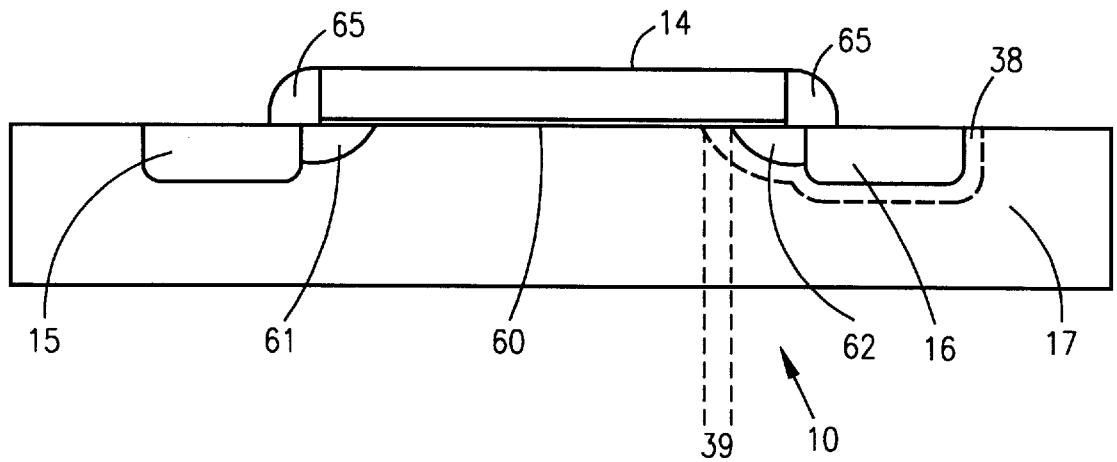
FIGS. 3a, 3b, and 3c are schematic illustrations of a MOS transistor which is tested in the device illustrated in FIG. 1 using a second method.
Figure 3B:
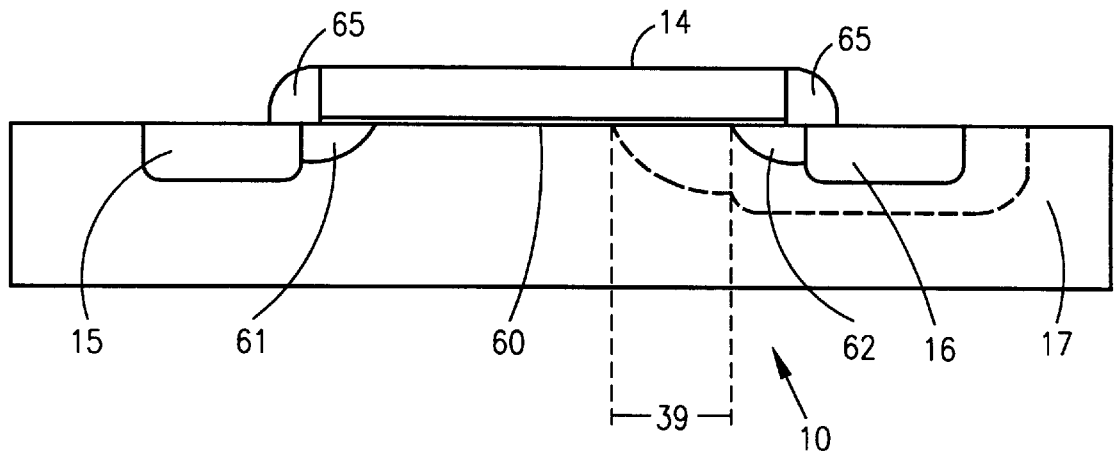
Figure 3C:
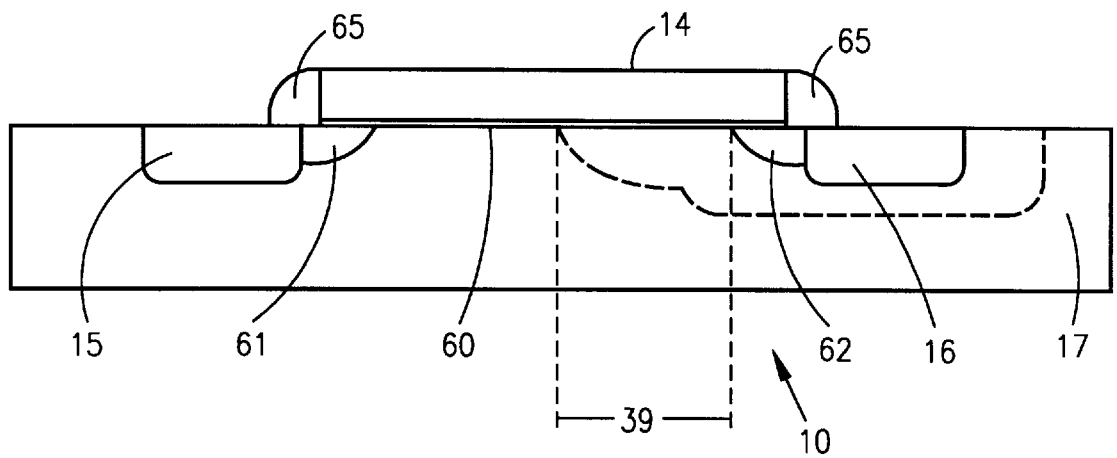

FIGS. 3a, 3b and 3c are schematic illustrations of the transistor 10 shown in FIG. 1 with depletion regions generated by different drain to substrate voltages $V_{DB}$. The measurement setup is not shown to simplify the figures. The transistor 10 being tested in this example is an NMOS. In an NMOS transistor, the drain/source depletion region shrinks with an applied negative drain/source to substrate voltage $V_{SB}/V_{DB}$ and expands with and applied positive drain/source to substrate voltage $V_{SB}/V_{DB}$ (the opposite behavior will be observed for PMOSFET's).

The controller 31 signals the drain variable DC power supply 23 to apply a series of increasing voltages, which increases the lengths of the depletion region 39 adjacent to the drain 16, as shown in FIGS. 3a, 3b, and 3c. FIGS. 3a, 3b, and 3c illustrate depletion regions 39 for the i−1, i, and i+1 values of the series of increasing voltages.

The controller 31 signals the drain variable DC power supply 23 to set the drain to substrate voltage to $V_{DB}(i-1)$, which causes the depletion region 38 adjacent to the drain 16, as shown in FIG. 3a. The controller 31 then signals the LCR meter 30 to measure the gate capacitance $C_{gb}(i-1)$, which is recorded by the controller 31.

The controller 31 signals the drain variable DC power supply 23 to increase the drain voltage to $V_{DB}(i)$, which increases the length of the depletion region 39 adjacent to the drain 16, as shown in FIG. 3b. The controller 31 then signals the LCR meter 30 to measure the gate capacitance $C_{gb}(i)$, which is recorded by the controller 31.

The controller 31 signals the drain variable DC power supply 23 to increase the drain voltage to $V_{DB}(i+1)$, which increases the length of the depletion region 39 adjacent to the drain 16, as shown in FIG. 3c. The controller 31 then signals the LCR meter 30 to measure the gate capacitance $C_{gb}(i+1)$, which is recorded by the controller 31.

One way of measuring effective channel length $L_{eff}$ is by setting $V_{SD}$ to the maximum negative value so that there is no depletion region. Then effective channel length $L_{eff}$ is defined as the length of the channel $L_c$. Using the measured gate capacity $C_{gb}(x)$ the controller is able to determine the channel length $L_c(x)=C_{gb}(x)/C_{ox}$. $L_{eff}=L_c(x)$ when there is no depletion region. There are other ways of measuring the effective channel length, such as the method described in "A New 'Shift and Ratio' Method for MOSFET Channel-Length Extraction", by Yuan Taur et al., IEEE Electron Device Letters. Vol 13, No: 5, May 1992, which can be used instead.

For $V_{DB}(x)$, the width of the depletion region 39 $W(x)=L_{eff}L_c(x)$, so that for $V_{DB}(i-1)$, $W(i-1)=L_{eff}-L_c(i-1)$, and for $V_{DB}(i)$, $W(i)=L_{eff}-L_c(i)$, and for $V_{DB}(i+1)$, $W(i+1)=L_{eff}-L_c(i+1)$.

Starting with the general equation $W(x)=L_{eff}-L_c(x)$ (Equation 3), we get:

$$\frac{dW}{dV_{DB}} = -\frac{dL_c}{dV_{DB}} \qquad \text{Equation 6}$$

For the point $V_{SD}(i)$, $dL_c/dV_{gd}$ can be estimated as:

$$\frac{dL(i)_c}{dV(i)_{DB}} \cong \frac{\Delta L(i)_c}{\Delta V(i)_{DB}} \cong \frac{L_c(i-1)-L_c(i+1)}{V_{DB}(i-1)-V_{DB}(i+1)} \qquad \text{Equation 7}$$

Equation 7

The controller 31 is then able to solve Equation 1 for $N_{ch}(i)$. The controller continues to take readings until the depletion region of the drain contacts the source extension so that the channel length $L_t$ approaches zero and the gate capacitance $C_{gb}$ drops abruptly. The controller 31 calculates $N_{ch}(x)$ for every measured $V_{DB}(x)$.

EXAMPLES

Figure 4:
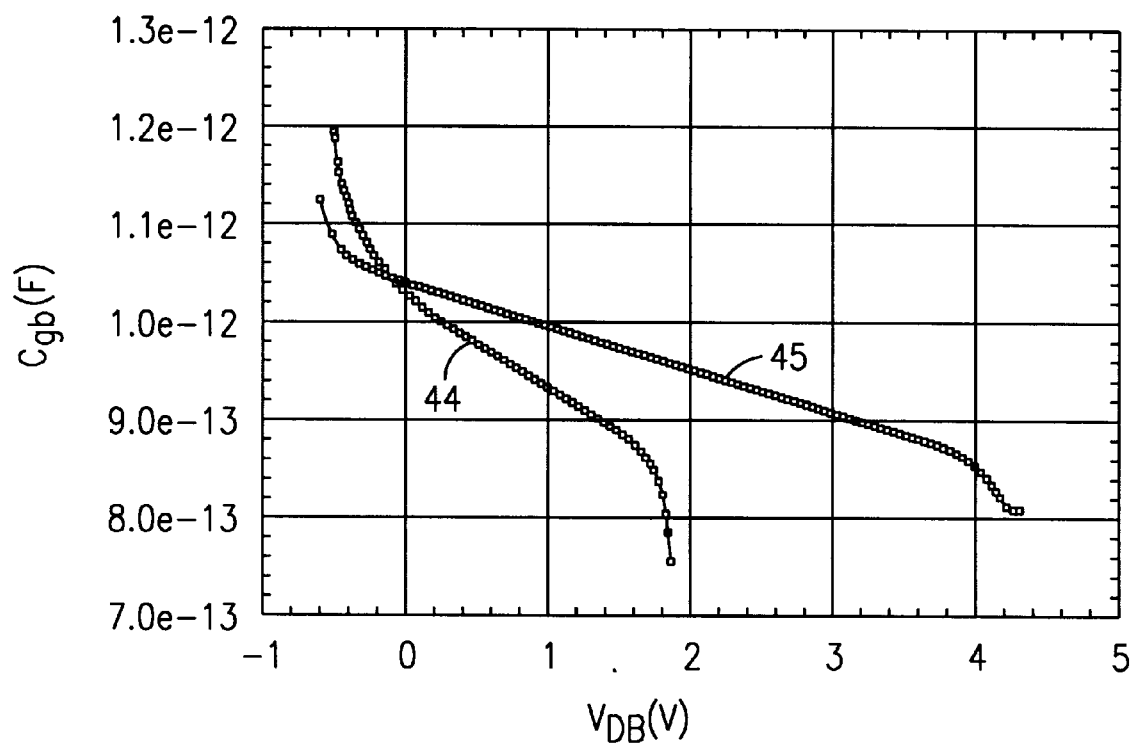
FIG. 4 is a graph of a typical MOS gate to substrate capacitance plotted against the voltage between the drain and the substrate of the MOS gate.

FIG. 4 is a graph plotting the gate capacitance $C_{gb}$ against the drain to substrate voltage $V_{DB}$. A source/drain measurement curve 44 is a plot of data for a MOS transistor measurement where the applied voltage to the source is equal to the applied voltage to the drain. A drain measurement curve 45 is a plot of data for a MOS transistor measurement where the applied voltage to the source is fixed and equal to zero. The slope of a curve at a point in FIG. 4 is $dC_{gb}/dV_{SD}=-C_{ox}dW/dV_{SD}$. These curves are examples of the relationship between gate capacitance and voltage applied between the source/drain and the substrate, and the relationship between the depletion width and voltage applied between the source/drain and the substrate. Using these plotted values, W(x) can be calculated, which can be plugged into Equation 1, to calculate $N_{ch}(x)$.

Figure 5:
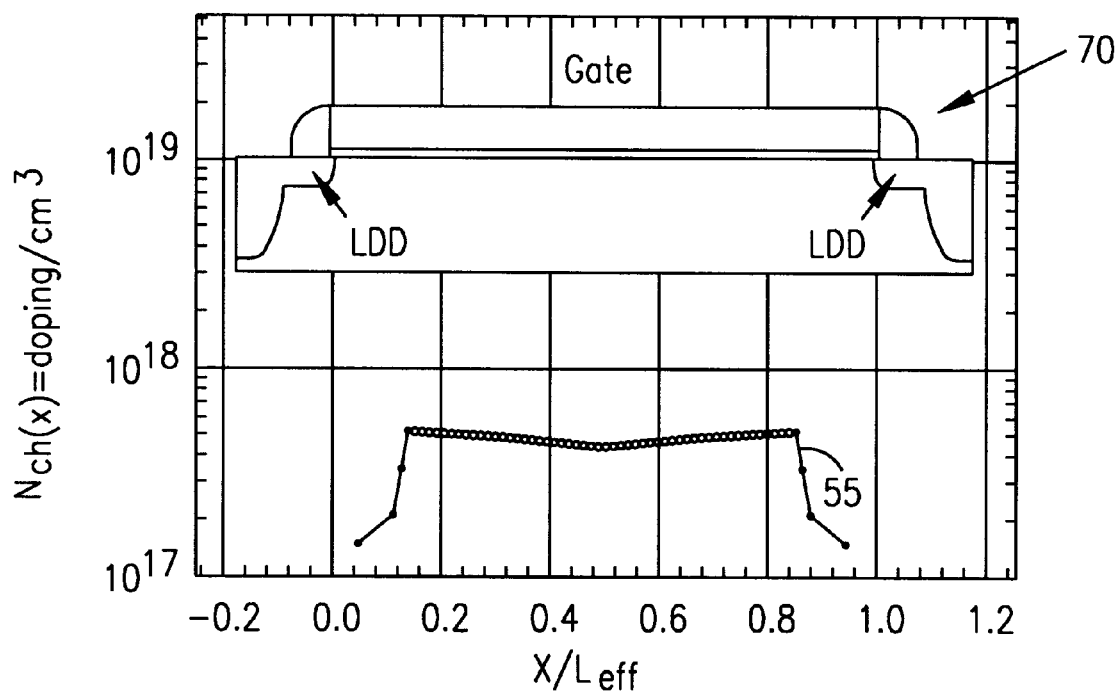
FIG. 5 is a graph of the doping profile obtained through the practice of the invention of a typical MOS gate without halo implantation.

FIG. 5 schematically illustrates a sample MOS transistor 70 that does not have halo implantation. Using the method described above, FIG. 5 also shows plotted curve 55, which plots x, a linear measurement along the length of the MOS transistor 70, against $N_{ch}(x)$ the lateral doping concentration. Curve 55 shows that the doping concentration under the gate of the MOS transistor 70 is reasonably constant.

Figure 6:
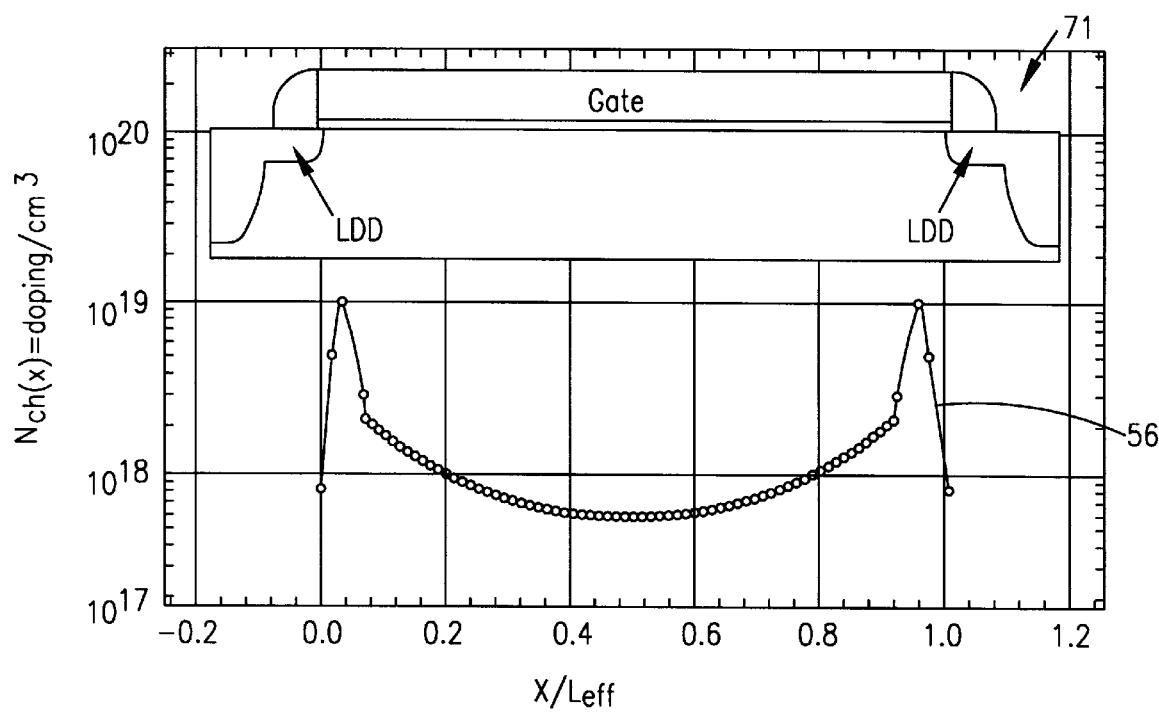
FIG. 6 is a graph of the doping profile obtained through the practice of the invention of a typical MOS gate with halo implantation.

FIG. 6 schematically illustrates another sample MOS transistor 71 that has halo implantation. Using the method described above FIG. 6 also shows plotted curve 56, which plots x, a linear measurement along the length of the MOS transistor 71, against $N_{ch}(x)$ the doping concentration. Curve 56 shows that the doping concentration near center of the channel is quite similar to the doping concentration of the MOS transistor 70 shown in FIG. 5. Curve 56 also shows that the MOS transistor 71 has very high peak doping peaks near the source and drain, which is due to the TED effect of the halo implantation.

Figure 7:
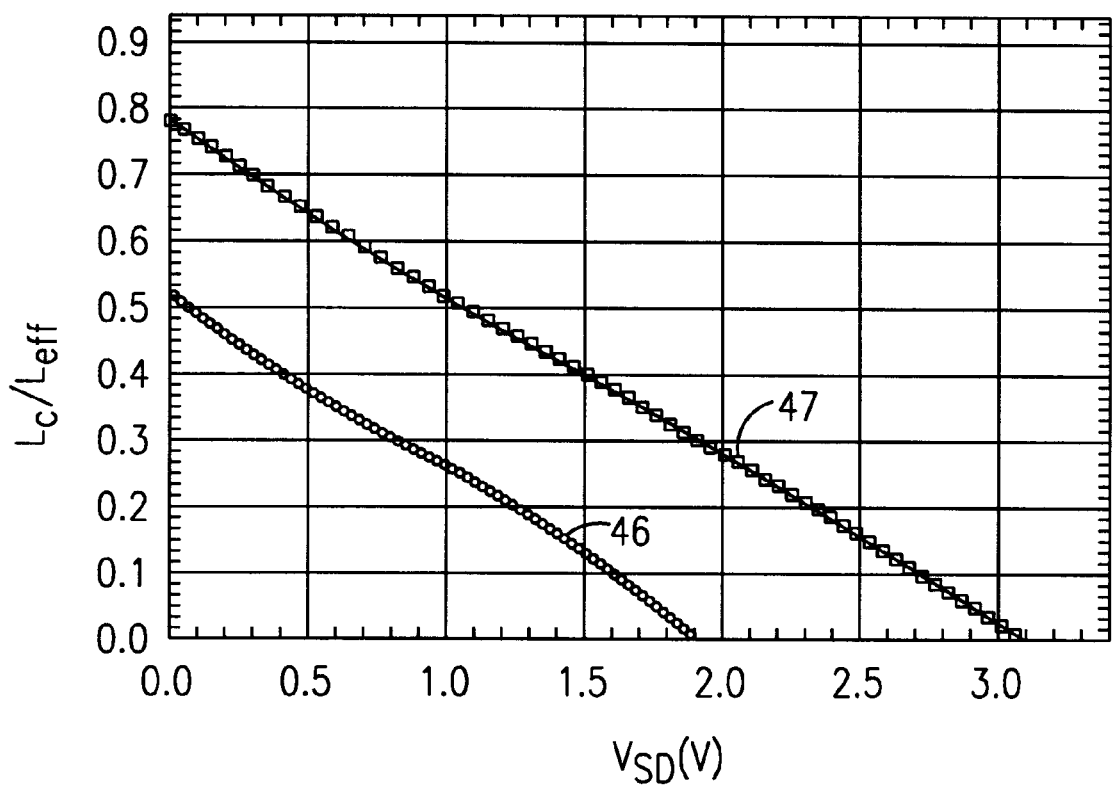
FIG. 7 is a graph of the extracted quasi-neutral channel length reduction of the drain junction depletion extension for MOSFET with and without halo doping.

FIG. 7 is a plot of the quasi-neutral channel length $L_c$ divided by the gate length $L_{eff}$ versus the second source drain voltage $V_{SD}$ with curve 46 plotting data from a non-halo doped device and curve 47 plotting data from a halo doped device. A higher $L_c$ and $V_{SD}$ margin is observed for the halo device, indicating improved short channel effect by using halo implantation. The voltage can either be applied between the source and the substrate or the drain and the substrate or both. For this reason in the claims, the notation first source/drain and second source/drain will be used. Under this notation, either the first source/drain can refer to the source, with the second source/drain referring to the drain, or the first source/drain can refer to the drain with the second source/drain referring to the source. In addition, in the claims the use of equation 1, also includes equations that are equivalent to equation 1, such as equations where capacitance is used instead of depletion width.

The present invention has been particularly shown and described with respect to certain preferred embodiments and features thereof. However, it should be readily apparent to those of ordinary skill in the art that various changes and modifications in form and detail may be made without departing from the spirit and scope of the inventions as set forth in the appended claims. The inventions illustratively disclosed herein may be practiced without any element which is not specifically disclosed herein.

We claim:

1. A method for measuring the lateral distribution of dopants along a channel, for a device with a first source/drain, a second source/drain, and a gate mounted on a substrate, comprising the steps of:
   applying a fixed voltage between the gate and the substrate;
   applying a series of different voltages between the first source/drain and the substrate;
   measuring capacitances between the gate and the substrate at the different voltages between the first source/drain and the substrate; and
   using the measured capacitances between the gate and the substrate at the different voltages between the first source/drain and the substrate to determine the channel doping concentration along the channel.

2. The method, as recited in claim 1, wherein the device has a known capacitance per unit length $C_{ox}$, and wherein the step of using the measured capacitances, comprises the steps of:
   using the measured capacitance to calculate the depletion width at a particular voltage of the series of different voltages; and
   using the depletion width for calculating channel doping concentration at a particular voltage of the series of different voltages.

3. The method, as recited in claim 2, wherein the step of using the depletion width for calculating channel doping concentration at a particular voltage of the series of different voltages, comprises the step of solving the equation $$N_{ch} = \frac{\varepsilon_s}{qW\frac{dW}{dV}}$$

to calculate the doping concentration at a particular voltage, where $N_{ch}$ is channel doping concentration, $\varepsilon_s$ the silicon dielectric permitivity, q the electron charge, W is the depletion width and dW/dV is the derivative of the depletion width with respect to the voltage applied between the first source/drain and the substrate.

4. The method, as recited in claim 3, wherein the step of using the measured capacitances to calculate the depletion width, comprises the steps of:
   calculating the channel length $L_c$ using the equation $L_c = C_{gb}/C_{ox}$, wherein $C_{gb}$ is one of the measured capacitances;
   measuring the effective length $L_{eff}$ of the device; and
   calculating the depletion width using the equation $W = L_{eff} - L_c$.

5. The method, as recited in claim 4, wherein the step of solving the equation, comprises the step of estimating dW/dV as ΔW/ΔV.

6. The method, as recited in claim 4, further comprising the step of applying a series of different voltages between the second source/drain and the substrate.

7. The method, as recited in claim 6, wherein the each voltage applied between the second source/drain and the substrate is equal to the voltage applied between the first source/drain and the substrate.

8. The method, as recited in claim 1, wherein the step of using the measured capacitance, comprises the step of solving the equation $$N_{ch} = \frac{\varepsilon_s}{qW\frac{dW}{dV}}$$

to calculate the doping concentration at a particular voltage of the series of different voltages, where $N_{ch}$ is channel doping concentration, $\varepsilon_s$ the silicon dielectric permitivity, q the electron charge, W is the depletion width and dW/dV is the derivative of the depletion width with respect to the voltage applied between the first source/drain and the substrate.

9. An apparatus for measuring the lateral distribution of dopants along a channel, for a device with a first source/drain, a second source/drain, and a gate mounted on a substrate, comprising:
   means for applying a series of different voltages between the first source/drain and the substrate;
   means for measuring capacitances between the gate and the substrate at the different voltages between the first source/drain and the substrate; and
   means for using the measured capacitances between the gate and the substrate at the different voltages between the first source/drain and the substrate to determine the doping concentration along the channel.

10. The apparatus, as recited in claim 9, wherein the device has a known capacitance per unit length $C_{ox}$, and wherein the means for using the measured capacitances, comprises:
    means for using the measured capacitance to calculate the depletion width at a particular voltage of the series of different voltages; and
    means for calculating channel doping concentration at a particular voltage of the series of different voltages.

11. The apparatus, as recited in claim 10, wherein the means for calculating channel doping at a particular voltage, comprises the means for solving the equation $$N_{ch} = \frac{\varepsilon_s}{qW\frac{dW}{dV}}$$

to calculate the channel doping concentration at a particular voltage, where $N_{ch}$ is channel doping concentration, $\varepsilon_s$ the silicon dielectric permitivity, q the electron charge, W is the depletion width and dW/dV is the derivative of the depletion width with respect to the voltage applied between the first source/drain and the substrate.

12. The apparatus, as recited in claim 11, wherein the means for using the measured capacitances to calculate the depletion width, comprises:
    means for calculating the channel length $L_c$ using the equation $L_c = C_{gb}/C_{ox}$, wherein $C_{gb}$ is one of the measured capacitances;

means for measuring the effective length $L_{\it{eff}}$ of the device; and means for calculating the depletion width using the equation $W=L_{\it{eff}}-L_c$.

13. The apparatus, as recited in claim 12, wherein the means for solving the equation, comprises means for estimating dW/dV as ΔW/ΔV.

14. The apparatus, as recited in claim 13, further comprising the means for applying a series of different voltages between the second source/drain and the substrate.

15. The apparatus, as recited in claim 14, wherein the each voltage applied between the second source/drain and the substrate is equal to the voltage applied between the first source/drain and the substrate.

16. The apparatus, as recited in claim 10, wherein the means for calculating channel doping at a particular voltage, comprises the means for solving the equation $$N_{ch} = \frac{\varepsilon_s}{qW\frac{dW}{dV}}$$

to calculate the channel doping concentration at a particular voltage, where $N_{ch}$ is channel doping concentration, $\varepsilon_s$ the silicon dielectric permitivity, q the electron charge, W is the depletion width and dW/dV is the derivative of the depletion width with respect to the voltage applied between the first source/drain and the substrate.

\* \* \* \* \*